US009452100B2

(12) United States Patent
Bigelow

(10) Patent No.: US 9,452,100 B2
(45) Date of Patent: Sep. 27, 2016

(54) PELVIC-ABDOMINAL SUPPORT GARMENT

(71) Applicant: Jill K. Bigelow, Los Angeles, CA (US)

(72) Inventor: Jill K. Bigelow, Los Angeles, CA (US)

( * ) Notice: Subject to any disclaimer, the term of this patent is extended or adjusted under 35 U.S.C. 154(b) by 78 days.

(21) Appl. No.: 14/358,022

(22) PCT Filed: Aug. 9, 2013

(86) PCT No.: PCT/US2013/054392
§ 371 (c)(1),
(2) Date: May 13, 2014

(87) PCT Pub. No.: WO2014/051863
PCT Pub. Date: Apr. 3, 2014

(65) Prior Publication Data
US 2014/0350509 A1      Nov. 27, 2014

Related U.S. Application Data

(60) Provisional application No. 61/683,517, filed on Aug. 15, 2012.

(51) Int. Cl.
*A61F 5/03*      (2006.01)
*A61F 13/14*     (2006.01)
(Continued)

(52) U.S. Cl.
CPC ............... *A61H 1/008* (2013.01); *A41C 1/08* (2013.01); *A61F 5/03* (2013.01); *A61F 7/08* (2013.01); *A61F 13/505* (2013.01); *A61F 2007/0022* (2013.01); *A61F 2013/1517* (2013.01);
(Continued)

(58) Field of Classification Search
CPC .................. A41C 1/08; A61F 13/505; A61F 2007/0022; A61F 2013/1517; A61F 5/03; A61F 5/24; A61F 5/28; A61F 13/148; A61F 7/02; A61F 5/30; A61F 5/0093; A61H 2205/083; A41D 13/1254
USPC ........ 602/61, 67, 68, 70, 73, 78; 2/326, 240, 2/466
See application file for complete search history.

(56) References Cited

U.S. PATENT DOCUMENTS 86,204 A  *  1/1869  Blake .......................... 128/100.1
3,174,482 A     3/1965  Parrott
(Continued)

FOREIGN PATENT DOCUMENTS

EP       2 198 818       6/2010
FR       2597332         10/1987
(Continued)

OTHER PUBLICATIONS

Webpage—FLA belt—Soft Form® Hernia Belt (1 pg.)—FLA Orthopedics (2004) http://flaorthopedics.com/srchproducts/abdominalsupports/34-630.pdf.
(Continued)

*Primary Examiner* — Peter S Vasat
(74) *Attorney, Agent, or Firm* — Karish & Bjorgum, PC

(57) ABSTRACT

A pelvic-abdominal support garment including a waist encircling band having shorts secured to the lower edge thereof, the shorts having a receptacle for receiving an ice pack, and a strap member secured at one end thereof to the back of said waist encircling band and the other end thereof attachable to the front of the waist encircling band after passing under the crotch region of the shorts to apply pressure to the crotch area of the wearer.

12 Claims, 8 Drawing Sheets

(51) Int. Cl.
*A61H 1/00* (2006.01)
*A41C 1/08* (2006.01)
*A61F 7/08* (2006.01)
*A61F 13/505* (2006.01)
*A61F 7/00* (2006.01)
*A61F 13/15* (2006.01)

(52) U.S. Cl.
CPC ..... *A61H2201/10* (2013.01); *A61H 2201/165* (2013.01); *A61H 2201/1647* (2013.01); *A61H 2205/083* (2013.01); *A61H 2205/085* (2013.01)

(56) References Cited

U.S. PATENT DOCUMENTS

| | | | |
|---|---|---|---|
| 3,783,879 | A | 1/1974 | Stalder |
| 4,416,272 | A | 11/1983 | Nelkin |
| 4,802,469 | A | 2/1989 | Gollestani |
| 5,300,058 | A * | 4/1994 | Goulait et al. ............... 604/391 |
| 5,571,039 | A | 11/1996 | Ford |
| 5,876,395 | A | 3/1999 | Hart et al. |
| 5,926,853 | A * | 7/1999 | Plank .............................. 2/406 |
| 6,080,125 | A | 6/2000 | Mott |
| 6,270,469 | B1 | 8/2001 | Mott |
| 6,308,341 | B1 * | 10/2001 | Shelton ............................ 2/400 |
| 6,422,242 | B1 | 7/2002 | Slautterback et al. |
| 6,575,342 | B1 | 6/2003 | Sundara et al. |
| 6,622,719 | B1 * | 9/2003 | Slautterback et al. ....... 128/98.1 |
| 7,425,171 | B2 | 9/2008 | Maupin |
| D628,300 | S | 11/2010 | Caden |
| 2002/0035747 | A1 * | 3/2002 | Kusibojoska et al. ............ 2/400 |
| 2005/0181705 | A1 | 8/2005 | Maupin |
| 2005/0229295 | A1 * | 10/2005 | Chun et al. ........................ 2/467 |
| 2006/0101558 | A1 * | 5/2006 | Coleman et al. .................. 2/400 |
| 2006/0247598 | A1 | 11/2006 | Roehrl et al. |
| 2007/0094775 | A1 | 5/2007 | Chun et al. |
| 2008/0254712 | A1 | 10/2008 | Christensen |
| 2009/0171259 | A1 | 7/2009 | Soerensen et al. |
| 2010/0094386 | A1 * | 4/2010 | Margolis et al. ............. 607/108 |
| 2010/0100019 | A1 | 4/2010 | Chen et al. |
| 2013/0158635 | A1 | 6/2013 | Federico et al. |

FOREIGN PATENT DOCUMENTS

| | | |
|---|---|---|
| JP | 2007215822 | 8/2007 |
| TW | M446624 | 2/2013 |

OTHER PUBLICATIONS

Webpage—FLA brief—Soft Form® Hernia Brief (1 pg.)—FLA Orthopedics (2004)—http://flaorthopedics.com/srchproducts/herniasupports/67-500.pdf.

Webpage—FLA_Binder—Preimum Woven Surgical Adominal Binders—(1 pg.)—FLA Orthopedics (2004) http://flaorthopedics.com/srchproducts/herniasupports/67-350.pdf.

Webpage—Fembrace/V-Brace (2 pgs.), (Jul. 23, 2013)—http://www.supportsockshop.com/V-Brace-by-Fembrace-Support-garments-for-Volvar-Varicosities-Genital-Prolapse-and-Incontinence-Style-6200-White-S.

* cited by examiner

PELVIC-ABDOMINAL SUPPORT GARMENT

CROSS-REFERANCE TO RELATED APPLICATIONS

The present application is a U.S. National Stage entry under 35 U.S.C. §371 of International Application No. PCT/US2013/054392, filed on 9 Aug. 2013, which claims benefit of U.S. Provisional Application No. 61/683,517, filed on 15 Aug. 2012, which is hereby incorporated by reference in its entierty.

RELATED APPLICATION

This is the nonprovisional application based upon Provisional Application Ser. No. 61/683,517, Filed Aug. 15, 2012 and Applicant claims the benefits of the filing date thereof.

BACKGROUND OF THE INVENTION

1. Field of the Invention

This invention is a pelvic-abdominal medical support garment for patient use to control pain, edema and infection occurring from acute or chronic conditions such as cancer or after genital or abdominal surgery or vaginal childbirth thereby reducing complications and improving recovery time.

2. Background of the Prior Art

Patients who have undergone aesthetic or reconstructive surgery of the abdomen, genitals or pelvis or who have given vaginal childbirth are likely candidates for some form of complications during the recovery period. Typical of such complications are atelectasis, hypostatic pneumonia, phlebitis, pulmonary complication, vulvar prolapse, abdominal swelling and lower back pain. Patients who have acute or chronic conditions such as cancer or severe arthritis often require support in the pelvic or abdominal areas to provide relief from pain. The prior art teaches the use of binders or girdles that use the elastic properties of fiber to provide abdominal support. Typical of such prior art are U.S. Pat. Nos. 3,783,879; 5,571,039 and 6,270,469. In some instances, the prior art offers back braces or belly braces and in some instances genital prolapse panties. The prior art teaches the utilization of both the elastic properties of the fibers used to form the garments and in some instances does teach the utilization of a non-elastic material to provide a mechanical support as opposed to the elastic support. There are also teachings in the prior art of panties that have integral pockets adapted to receive cold packs to assist in pain relief.

The prior art support garments currently known however do not provide a garment which can be immediately worn by the patient and which provides the ability to easily adjust the amount of pressure that is to be applied to the crotch region of the user nor is there any device which also allows the user to apply ice and an absorbent pad to the crotch region of the user to provide the desired support, increase the comfort of the crotch area and provide early ambulation to help the patient reestablish his or her normal physiology and prevents or minimizes complications.

SUMMARY OF THE INVENTION

A pelvic-abdominal support garment including a waist encircling member which is adjustably securable by the user, shorts secured to the bottom edge of the waistband with the shorts defining a crotch region, and a strap member having one end thereof secured to the back portion of the waist encircling member and the other end thereof attachable by the user to the front of the waist encircling member after passing under the crotch region of the shorts so that the strap applies pressure, adjustable by the user, to the crotch area of the wearer.

DETAILED DESCRIPTION OF THE PREFERRED EMBODIMENT OF THE INVENTION

Figure 1:
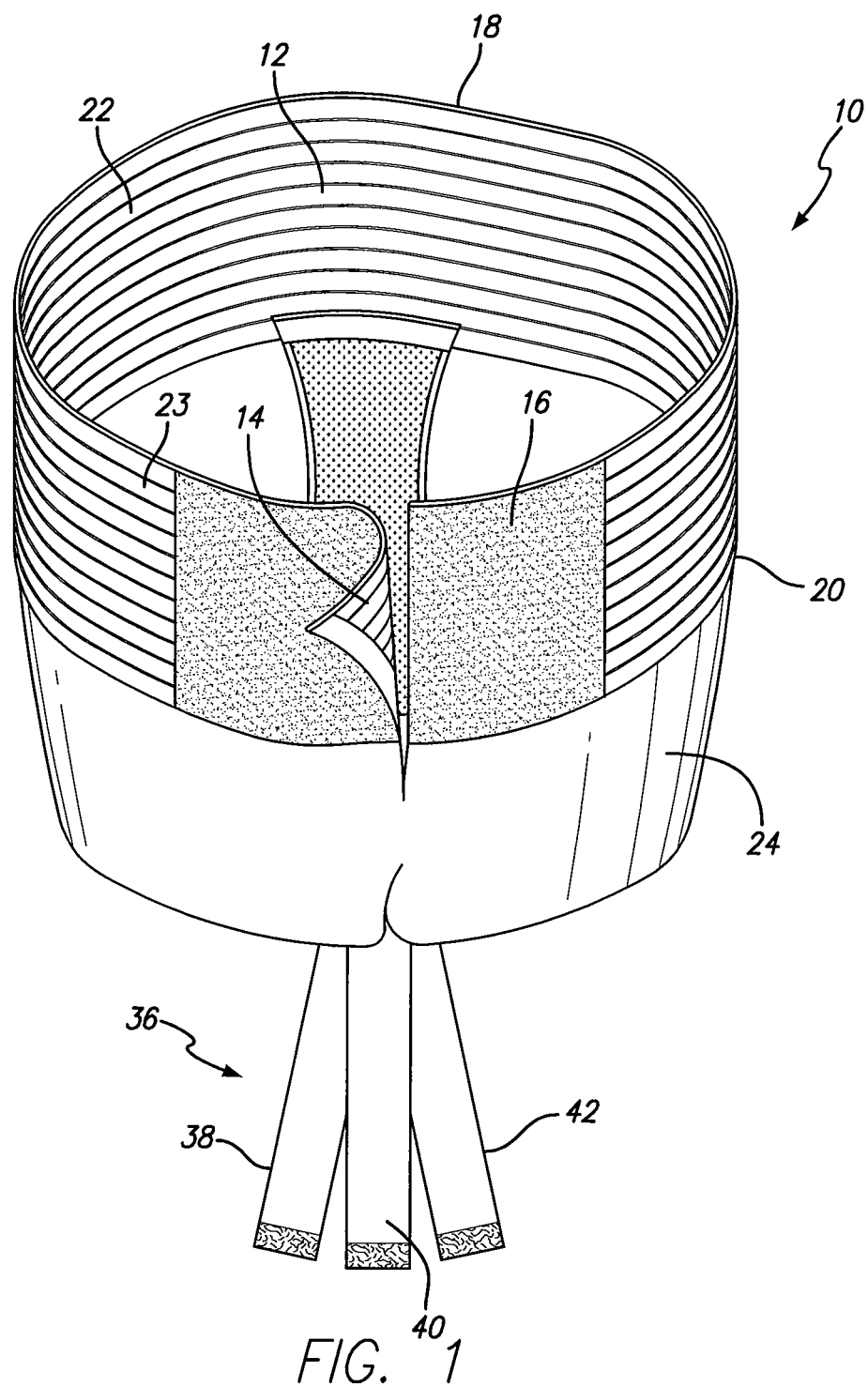
FIG. 1 is a perspective view of the medical support garment constructed in accordance with the principles of the present invention shown open.
Figure 2:
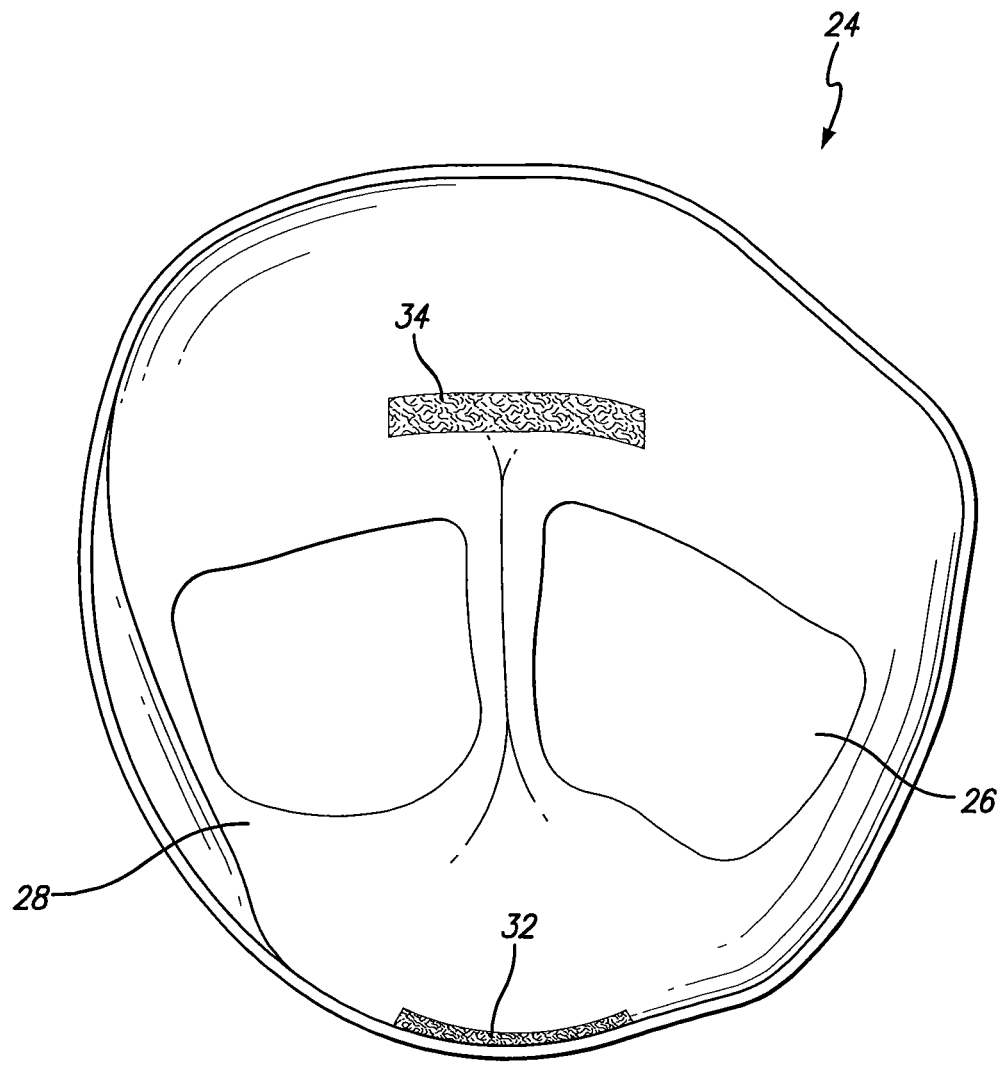
FIG. 2 is a perspective view of shorts detached from the garment.

As referred to above, patients who have acute or chronic conditions such as cancer or severe arthritis or who have undergone aesthetic or reconstructive surgery of the abdomen, genitals or pelvis or women who have given vaginal childbirth often experience severe discomfort, swelling, vulvar prolapse, abdominal swelling, joint pain and lower back pain. The pelvic-abdominal medical support garment of the present invention has an upper adjustable waist encircling member which extends from approximately the top of the hip bone to the upper abdominals and is made from a stiff supportive brace-like material which is designed to support the back, the abdominals and to place pressure on the abdominal cavity to reduce swelling. The bottom part of the garment is a shorts-style garment made from antibacterial and quick-dry material which also has the capability of stretching and is non-removably secured to the lower edge of the upper adjustable waist encircling member. The shorts-style portion of the garment includes a removable member having a pocket or receptacle attachable to the crotch region thereof for holding a frozen or heated gel pack to apply cold or heat to the crotch area of the wearer. The removable member having the pocket is also adapted to receive an absorbent pad. An elastic strap is secured to the rear portion of the waist encircling member and passes under the crotch region of the shorts with the opposite end of the elastic strap being attachable by a hook and loop fastener to the front portion of the waist encircling member so that pressure can be applied against the crotch of the wearer in an amount adjustable by the wearer.

A pelvic-abdominal adjustable medical support garment of the present invention addresses the various issues faced by a patient with one device that can be worn immediately after surgery or after giving birth and over underclothing for weeks thereafter providing support to the back, abdominals and vulva while the patient is recovering.

Referring now to the drawings and more particularly to FIGS. 1 through 4, the pelvic-abdominal medical support garment 10 is illustrated. As is therein shown, the garment includes a waist encircling member 12 which has an opening 14 so that when the user steps into the garment 10 as will be described more in detail hereinbelow, the waist encircling member may be closed and secured at the opening portions 14 and 16 by a hook and loop fastener such as the type sold under the trademark Velcro. The garment 10 has a top edge 18 and a bottom edge 20 as well as a back portion 22 and a front portion 23. The waist encircling member 12 of the garment 10 is constructed from a stiff supportive brace-like material which is laterally elastic but longitudinally unelastic. This stiff supportive brace-like material supports the back and the abdominals and the lateral elasticity places adjustable pressure on the abdominal cavity. When the waist encircling member is placed in position, the wearer may by bringing the two parts of the opening 14 and 16 together apply the desired amount of pressure to the abdominal cavity at the time the hook and loop fasteners are secured.

Shorts 24 made of a stretchable material are non-removably secured to the bottom edge 20 of the waist encircling member 12. The shorts 24 have leg openings 26 and 28 so the user may step into the shorts. The shorts also include a crotch region 30 which is adapted to engage the crotch region of the wearer. The interior of the shorts 24 has secured thereto one-half of a hook and loop fastener as shown at 32 and 34. These portions of the hook and loop fastener 32 and 34 are situated at each end of the crotch region 30 of the shorts and are adapted to receive a detachable member having a pocket or receptacle as will be described more fully below.

Figure 3:
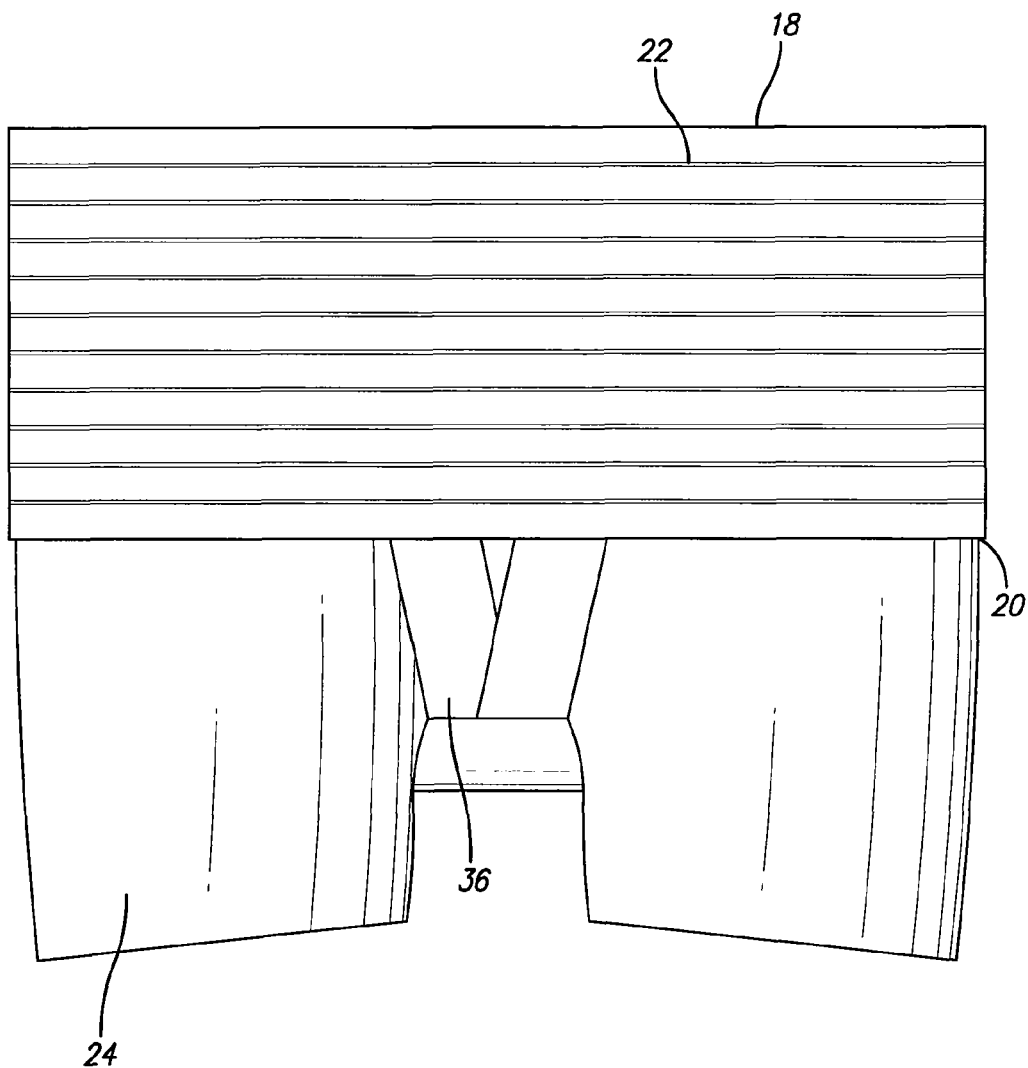
FIG. 3 is a rear view of the garment.
Figure 4:
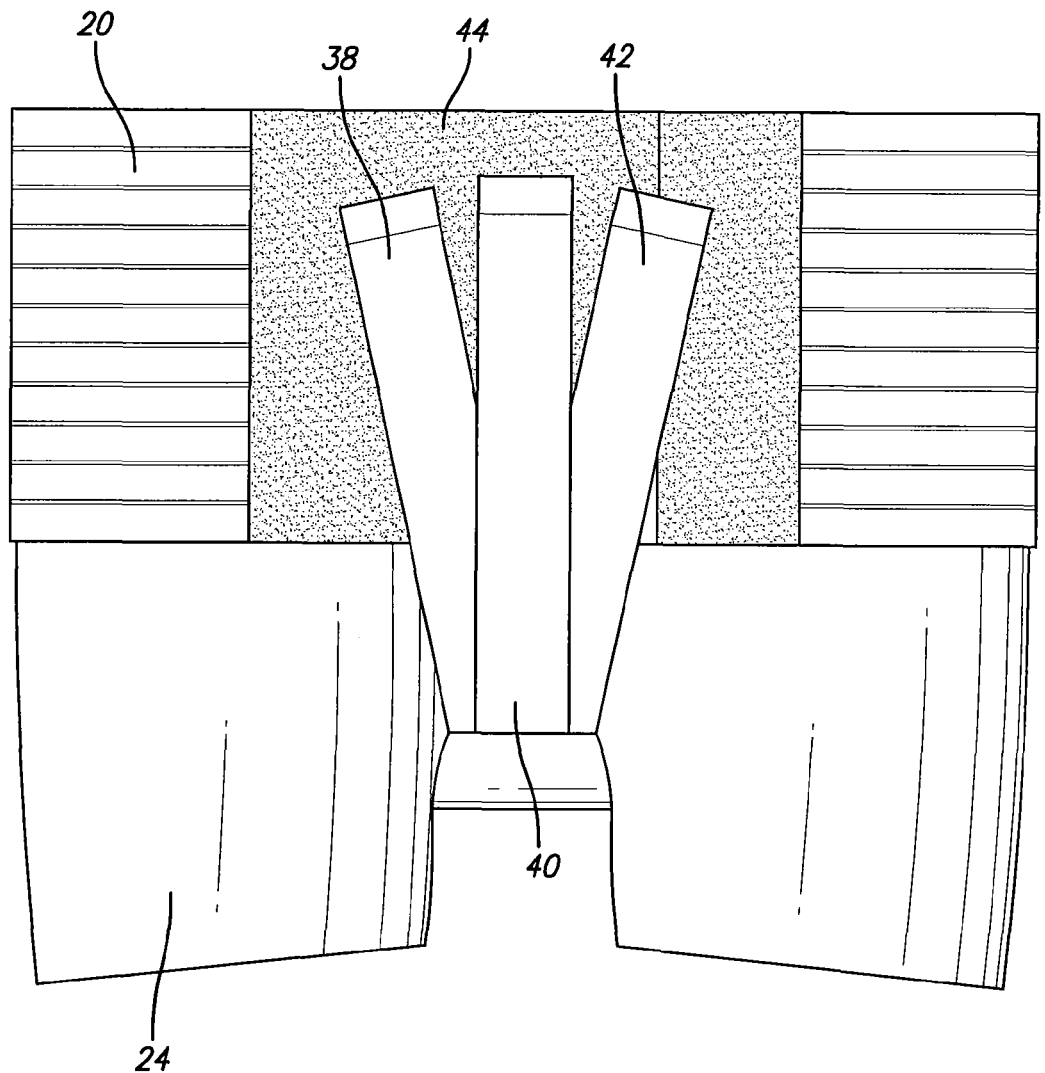
FIG. 4 is a front view thereof.

A strap member 36 is secured to the back 22 of the waist encircling member adjacent the lower edge 20 thereof As illustrated, particularly in FIGS. 1, 3 and 4, the strap member 36 preferably includes three separate and distinct straps, 38, 40 and 42. These straps are elastic and when the wearer has the garment in place, the strap member 36 is passed under the crotch 30 of the shorts on the outside thereof and are brought to the front 23 of the waist encircling member 12. The front portion 23 of the waist encircling band is constructed as one half a hook and loop fastener such as Velcro and such is illustrated at 44 in FIG. 4. As can be seen, particularly in FIG. 4, the three straps 38, 40 and 42 may be pulled upwardly by the wearer and then positioned with the central strap at the center and the two straps 38 and 42 placed laterally from the first strap 40, thus applying pressure to the crotch area of the wearer in a particular pattern that is more comfortable for the wearer and yet applies the desired amount of pressure to the crotch region to provide the desired amount of support.

It will now be recognized that when the wearer wishes to utilize the support garment 10, the wearer may simply separate the waist encircling member by separating the two portions 14, 16 by separating the hook and loop fastener and then step into the shorts by placing the user's feet and legs through the openings 26 and 28 in the shorts 24. The shorts are made from elastic material which is antibacterial and quick dry.

Figure 5:
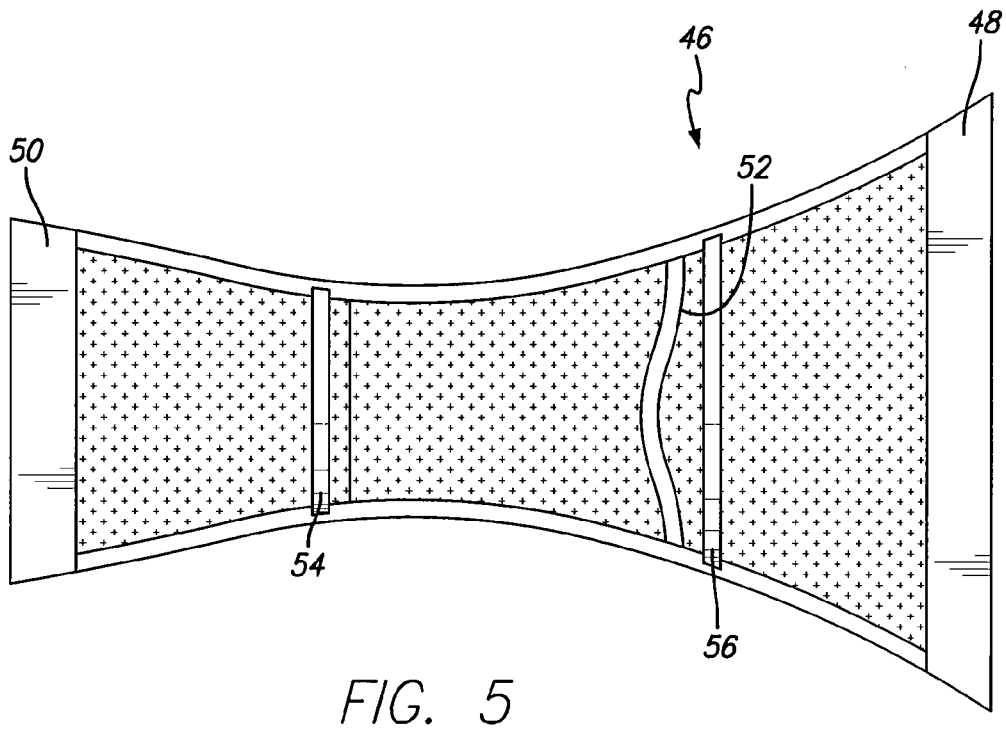
FIG. 5 illustrates a detachable member including a pocket or receptacle for receiving a frozen gel pack.

Referring now more specifically to FIG. 5, there is illustrated a separate detachable member 46 which has secured to each end thereof at 48 and 50 the other half of the hook and loop fastening material which cooperates with the first half thereof as shown at 32 and 34 adjacent the crotch region of the shorts 24. The detachable member 46 is constructed such that a pocket or receptacle 52 is formed therein. The pocket 52 would extend along a portion of the member 46 and is adapted to receive a frozen or heated gel pack so that when the member 46 is positioned internally of the crotch region of the shorts 24, cold or heat may be applied through the utilization of the frozen or heated gel pack to the crotch region of the wearer. Since the member 44 is detachable from the shorts, the member 46 may be washed and cleaned periodically as desired or more than one such member may be provided to the user.

Figure 6:
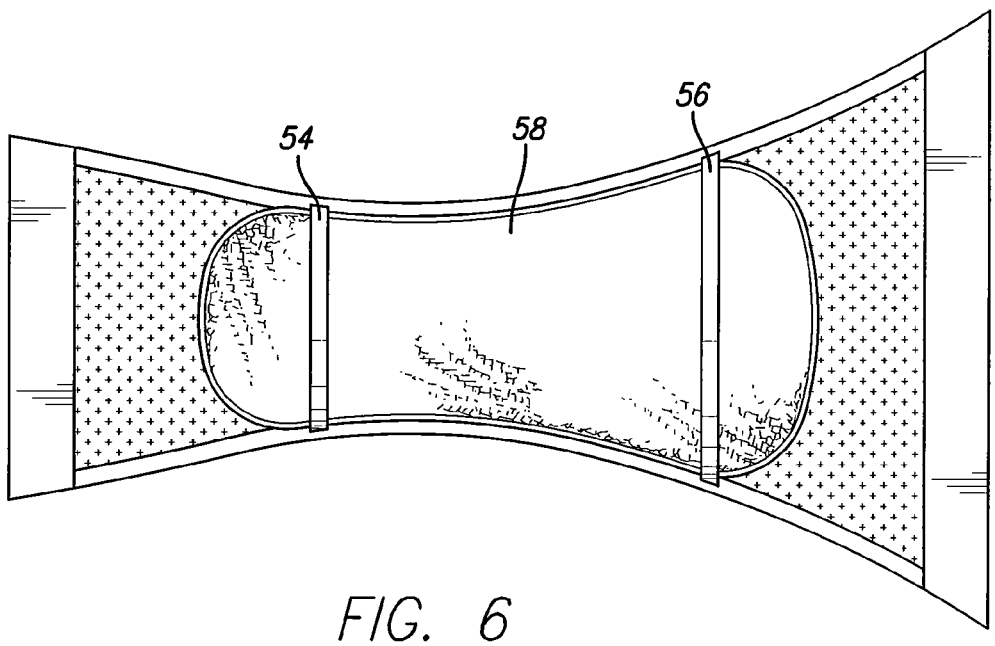
FIG. 6 shows the detachable member adapted to receive an absorbent pad.

As is also shown in FIGS. 5 and 6, the member 46 has a first strap or cord 54 positioned toward one end thereof and an additional strap or cord 56 adjacent the opposite end. The cords 54 and 56 are utilized to retain an absorbent pad 58 which would be positioned immediately adjacent the crotch of the wearer. It should be understood that the gel pack may be inserted into the pocket 52 of the member 46 and thereafter the pad 58 positioned by inserting it underneath the two straps 54 and 56 to secure it in place. If desired, the pad may also have an adhesive surface which would be placed against the inner surface of the member 46 to assist in securing it in place on the member 46. The pad may also be secured by a hook and loop fastener.

Figure 7:
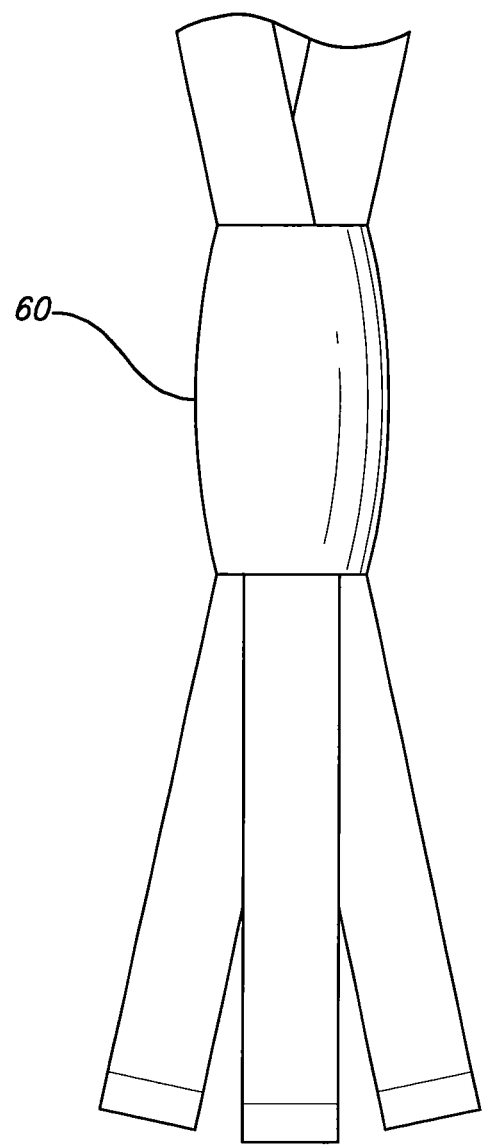
FIG. 7 illustrates a strap member having a pad around the crotch receiving area thereof.

As previously indicated, the strap member 36 preferably includes three separate straps 38, 40 and 42. To make these straps more comfortable for the user, a pad 60 as shown in FIG. 7 is provided to encircle the straps 38, 40 and 42 and to be positioned at the crotch area of the user to thereby provide a padded area between the straps and the crotch area of the user.

Figure 8:
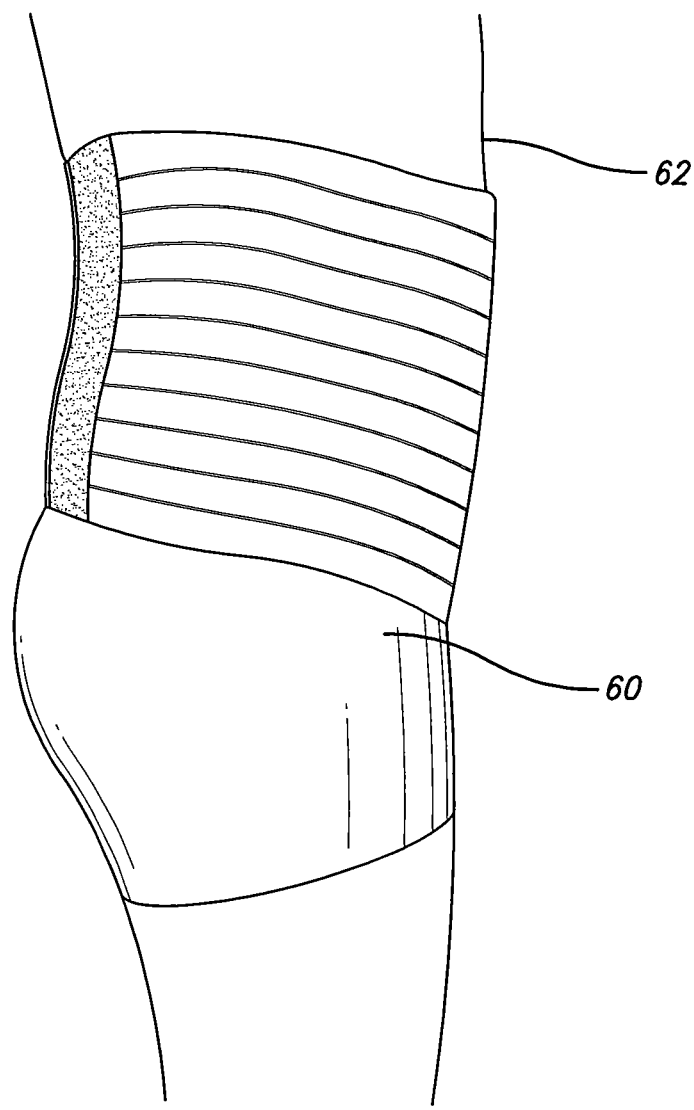
FIG. 8 is a side view of a wearer having the support garment of the present invention thereon.

As shown more clearly in FIG. 8, the pelvic-abdominal support garment 10 when in place on the body of a user extends from the upper hip area 60 to the upper abdominal area 62 of the user.

Figure 9:
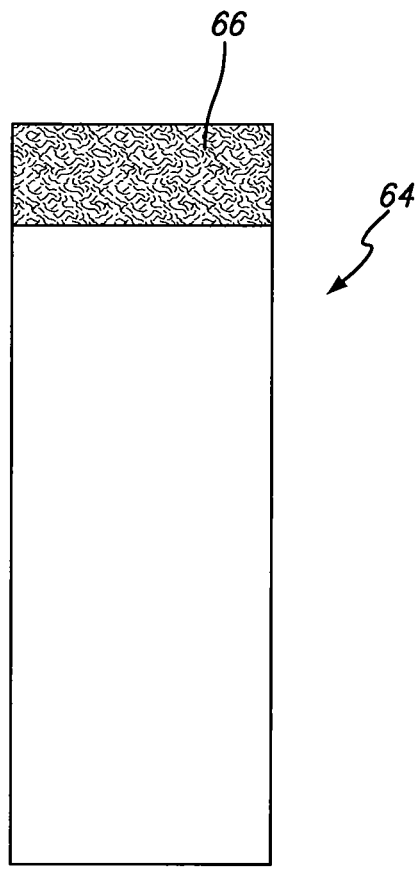
FIG. 9 is a detachable member adapted to receive a foreign gel pack and is attachable to the outside of the garment at front or back.
Figure 10:
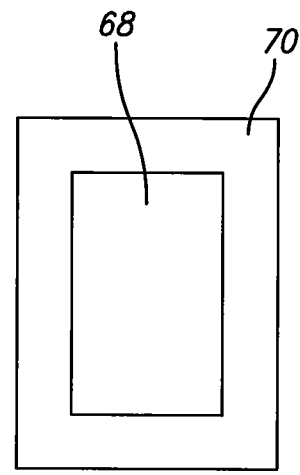
FIG. 10 is a view of the member of FIG. 9 showing the pocket to receive the frozen gel pack.

Referring now more particularly to FIG. 9, there is illustrated a detachable member 64 which has a hook and loop fastener section 66 at the top thereof The fastener 66 is attachable to the waist circling member 12 at the top of either the front or the back thereof By reference to FIG. 10, there is shown a pocket 68 on the reverse side 70 of the member 64. A frozen or heated gel pack may be inserted into the pocket 68 and then the member 64 is folded over so the gel pack is against a desired part of the user's back or abdomen to apply cold or heat thereto.

In some instances, for example, such as immediately after surgery or childbirth, when body exude from incisions may soil a garment yet it is desired to apply pressure and cold or heat to the area, the pelvic-abdominal support garment of the present invention may be constructed of non-durable materials which may be discarded after use. For example, the garment of the present invention could be constructed of Pampers Swaddlers diaper-like material which has absorbent capability and is stretchable and has overlapping areas to secure the garment in place. In such instances the pocket for receipt of the gel pack may be formed as a part of the crotch of the garment.

There has thus been disclosed a pelvic-abdominal medical device support garment which is useful to provide support and comfort to a wearer to aid in the recovery of the wearer after surgery or vaginal delivery of a child or to provide relief from acute or chronic medical conditions.

What is claimed is:

1. A pelvic-abdominal support garment comprising:
   a combination of a waist encircling member and shorts integrated into a support garment, said waist encircling member having a top edge, a bottom edge, a front portion and a back portion, the front portion having an opening configured to be closed and secured by a wearer, the waist encircling member extending between the top and bottom edges by an amount adapted to cover substantially all of the front and back of the waist area of the wearer, the waist encircling member being laterally elastic and longitudinally substantially non-elastic whereby when the wearer closes and secures the opening in the front portion of the waist encircling member it is adapted to place adjustable pressure on the wearer's abdominal region, said waist encircling member includes one-half of a hook and loop fastener at least on an outer facing side of the front portion thereof;

said shorts being non-removably secured to the bottom edge of said waist encircling member and having a crotch region;

a detachable member defining a receptacle for holding a gel-pack adapted to apply cold or heat to the crotch area of the wearer secured by a hook and loop fastener to the interior of the crotch region of the shorts; and a strap member having one end thereof secured to the back portion of said waist encircling member and the other end thereof attachable to the one half of a hook and loop fastener on the front portion of said waist encircling member after passing under the crotch region of said shorts by another half of a hook and loop fastener on said strap member so that the strap member is adapted to apply pressure to the crotch area of the wearer.

2. A pelvic-abdominal support garment as defined in claim 1 wherein said shorts are constructed of a stretchable material.

3. A pelvic-abdominal support garment as defined in claim 1 wherein said waist encircling member is constructed of a stiff supportive material which is adapted to provide support to the back and abdominal region of the wearer.

4. A pelvic-abdominal support garment as defined in claim 1 wherein the crotch region of said shorts includes means for securing an absorbent pad therein.

5. A pelvic-abdominal support garment as defined in claim 4 wherein said means for securing the absorbent pad includes a hook and loop fastener.

6. A pelvic-abdominal support garment as defined in claim 1 wherein said other end of said strap member is divided into a plurality of sections so the wearer can adjust the manner in which pressure is applied to the crotch area of the wearer.

7. A pelvic-abdominal support garment as defined in claim 6 wherein the portion of said strap member contacting the crotch region of said shorts includes a padded member surrounding the strap member.

8. A pelvic-abdominal support garment as defined in claim 1 wherein said strap member is a plurality of straps.

9. A pelvic-abdominal support garment as defined in claim 8 which includes three straps so that the wearer can secure the other end of one strap to a central portion of the front portion of said waist encircling member and can secure the other end of the remaining two straps laterally displaced from the other end of said one strap.

10. A pelvic-abdominal support garment as defined in claim 8 wherein a padded member surrounds the plurality of straps where they contact the crotch region of the shorts.

11. A pelvic-abdominal support garment as defined in claim 1 wherein said support garment is constructed of non-durable disposable material configured to be discarded after use.

12. A pelvic-abdominal support garment as defined in claim 1 which further includes a second detachable member having first and second sides and having a hook and loop fastener section at one end thereof on said first side and a pocket in said second side for receiving a gel pack, said second detachable member being securable to said waist encircling member at the outer facing side proximal to the top edge thereof and folded over to the interior facing side thereof and adapted to apply cold or heat to the waist area of the wearer of the garment.

\* \* \* \* \*